(12) United States Patent
Gong

(10) Patent No.: US 7,081,531 B2
(45) Date of Patent: Jul. 25, 2006

(54) BRIDGED BICYCLIC AMINE DERIVATIVES USEFUL AS CCR-3 RECEPTOR ANTAGONISTS

(75) Inventor: Leyi Gong, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 157 days.

(21) Appl. No.: 10/787,921

(22) Filed: Feb. 26, 2004

(65) Prior Publication Data

US 2004/0176416 A1    Sep. 9, 2004

Related U.S. Application Data

(60) Provisional application No. 60/450,380, filed on Feb. 27, 2003.

(51) Int. Cl.
*C07D 471/18* (2006.01)
*C07D 451/04* (2006.01)
*C07D 487/18* (2006.01)

(52) U.S. Cl. .................. 540/477; 546/94; 548/428

(58) Field of Classification Search .................. None
See application file for complete search history.

(56) References Cited

U.S. PATENT DOCUMENTS 4,366,154 A * 12/1982  Tomesch .................. 514/63

6,342,509 B1  1/2002  Hirschfeld et al.

FOREIGN PATENT DOCUMENTS

| EP | 0 013 138 B1 | 12/1983 |
|---|---|---|
| EP | 0 903 349 A2 | 3/1999 |
| WO | WO 94/22846 A1 | 10/1994 |
| WO | WO 00/29377 A1 | 5/2000 |
| WO | WO 00/31033 A1 | 6/2000 |
| WO | WO 01/29000 A2 | 4/2001 |
| WO | WO 02/26708 A1 | 4/2002 |

* cited by examiner

*Primary Examiner*—Cecilia Tsang
*Assistant Examiner*—Lexington A. Hoffman
(74) *Attorney, Agent, or Firm*—Grant D. Green

(57) ABSTRACT

Compounds having the formula (I), $$Ar—(F)-(E)-(CR^3R^4)—(CHR^5)_m-(T)-(Q)-Ar^1,$$

are useful as CCR-3 receptor antagonists, wherein T is a bridged heterocyclyl group having one N atom and a bridge of one to two bridgehead carbon atoms; Ar and $Ar^1$ are aryl or heteroaryl; F is alkylene, alkenylene, or a bond; E is $—C(=O)N(R^{10})—$, $—SO_2N(R^{10})—$, $—N(R^{11})C(=O)N(R^{10})—$, $—N(R^{11})SO_2N(R^{10})—$, $—N(R^{11})C(=S)N(R^{10})—$, $—N(R^{11})C(=O)—$, $—N(R^{11})SO_2—$, $—N(R^{12})C(=O)CH(R^{13})—$, or $CH(R^{13})C(=O)N(R^{12})—$; Q is $—C(=O)—$ or $C_{1-2}$alkylene; and $R^3$, $R^4$, $R^5$, $R^9$, $R^{10}$, $R^{11}$, $R^{12}$, and $R^{13}$ are defined as set forth in the specification.

18 Claims, No Drawings

BRIDGED BICYCLIC AMINE DERIVATIVES USEFUL AS CCR-3 RECEPTOR ANTAGONISTS

PRIORITY

This application claims priority from U.S. Ser. No. 60/450,380, filed 27 Feb. 2003, incorporated herein by reference in full.

FIELD OF THE INVENTION

The invention relates to certain bridged bicyclic amine derivatives that are CCR-3 receptor antagonists, as well as pharmaceutical compositions containing them and methods for their use.

BACKGROUND INFORMATION

Tissue eosinophilia is a feature of a number of pathological conditions such as asthma, rhinitis, eczema and parasitic infections (see Bousquet, J. et al., *N. Eng. J. Med.* 323: 1033–39 (1990) and Kay, A. B. and Corrigan, C. J., *Br. Med. Bull.* 48:51–64 (1992)). In asthma, eosinophil accumulation and activation are associated with damage to bronchial epithelium and hyperresponsiveness to constrictor mediators. Chemokines such as RANTES, eotaxin and MCP-3 are known to activate eosinophils (see Baggiolini, M. and Dahinden, C. A., *Immunol. Today,* 15:127–33 (1994), Rot, A. M. et al., *J. Exp. Med.* 176:1489–95 (1992) and Ponath, P. D. et al., *J. Clin. Invest.,* 97(3):604–12 (1996)). However, unlike RANTES and MCP-3 which also induce the migration of other leukocyte cell types, eotaxin is selectively chemotactic for eosinophils (see Griffith-Johnson, D. A. et al., *Biochem. Biophy. Res. Commun.* 197:1167 (1993), and Jose, P. J. et al., *Biochem. Biophy. Res. Commun.* 207:788 (1994)). Specific eosinophil accumulation has been observed at the site of administration of eotaxin, whether by intradermal or intraperitoneal injection or aerosol inhalation (see Griffith-Johnson, D. A. et al., supra; Jose, P. J. et al., supra; Rothenberg, M. E. et al., *J. Exp. Med.* 181:1211 (1995), and Ponath, P. D., supra).

Glucocorticoids such as dexamethasone, methprednisolone and hydrocortisone have been used for treating many eosinophil-related disorders, including bronchial asthma (R. P. Schleimer et al., *Am. Rev. Respir. Dis.,* 141:559 (1990)). The glucocorticoids are believed to inhibit IL-5 and IL-3 mediated eosinophil survival in these diseases. However, prolonged use of glucocorticoids can lead to side effects in patients such as glaucoma, osteoporosis, and growth retardation (see Hanania, N. A. et al., *J. Allergy and Clin. Immunol.,* 96:571–79 (1995) and Saha, M. T. et al., *Acta Paediatrica,* 86(2):138–42 (1997)). It is therefore desirable to have an alternative means of treating eosinophil-related diseases without incurring these undesirable side effects.

Recently, the CCR-3 receptor was identified as a major chemokine receptor that eosinophils use for their response to eotaxin, RANTES and MCP-3. When transfected into a murine pre-beta lymphoma line, CCR-3 bound eotaxin, RANTES and MCP-3 conferred chemotactic responses on these cells to eotaxin, RANTES and MCP-3 (see Ponath, P. D. et al., *J. Exp. Med.,* 183:2437–48 (1996)). The CCR-3 receptor is expressed on the surface of eosinophils, T-cells (subtype Th-2), basophils and mast cells and is highly selective for eotaxin. Studies have shown that pretreatment of eosinophils with an anti-CCR-3 mAb completely inhibits eosinophil chemotaxis to eotaxin, RANTES and MCP-3 (see Heath, H. et al., *J. Clin. Invest.,* 99(2):178–84 (1997)). U.S. Pat. Nos. 6,140,344 and 6,166,015 issued to Applicant herein and EP application EP903349, published Mar. 24, 1999 disclose CCR-3 antagonists that inhibit eosinophilic recruitment by chemokine such as eotaxin.

SUMMARY OF THE INVENTION

The present invention is directed to bridged cyclic amine derivatives useful as CCR3 receptor antagonists which are capable of inhibiting the binding of eotaxin to the CCR-3 receptor and thereby provide a means of combating eosinophil induced diseases, such as asthma.

In a first aspect, this invention provides a compound of Formula (I):

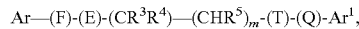

wherein:

T is

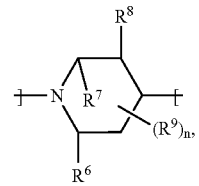

where $R^6$ is taken together with one of $R^7$ and $R^8$ to form a bridge of one to two bridgehead carbon atoms, and the other of $R^7$ and $R^8$ is selected from hydrogen and $R^9$;

Ar and $Ar^1$ are, independently of each other, aryl or heteroaryl;

F is alkylene, alkenylene, or a bond;

E is selected from —C(=O)N($R^{10}$)—, —SO$_2$N($R^{10}$)—, —N($R^{11}$)C(=O)N($R^{10}$)—, —N($R^{11}$)SO$_2$N($R^{10}$)—, —N($R^{11}$)C(=S)N($R^{10}$)—, —N($R^{11}$)C(=O)—, —N($R^{11}$)SO$_2$—, —N($R^{12}$)C(=O)CH($R^{13}$)—, and CH($R^{13}$)C(=O)N($R^{12}$)—, where:

$R^{10}$, $R^{11}$, $R^{12}$, and $R^{13}$ are, independently of each other, hydrogen, alkyl, acyl, haloalkyl, cycloalkyl, cycloalkylalkyl, aryl, aralkyl, aralkenyl, heteroaryl, heteroaralkyl, heterocycloalkyl, heteroalkyl, or -(alkylene)-C(=O)-Z, where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

or alternatively, $R^{12}$ and $R^{13}$ may be taken together with the nitrogen and carbon atoms to which they are attached, respectively, to form a heterocyclyl or heteroaryl ring optionally substituted with up to two groups selected from $R^{14}$;

$R^3$ and $R^4$ are, independently of each other, hydrogen, alkyl, alkenyl, haloalkyl, cycloalkyl, cycloalkylalkyl, aryl, aralkyl, heteroaryl, heteroaralkyl, heterocyclyl, heterocyclylalkyl, heteroalkyl, -(alkylene)-C(=O)-$Z^1$, or -(alkylene)-C(O)$_2Z^1$, where $Z^1$ is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

$R^5$ is hydrogen or alkyl;

Q is —C(=O)— or $C_{1-2}$alkylene;

$R^9$ is attached to any available carbon atom of ring T and is selected from lower alkyl, hydroxy, lower alkoxy, halo, cyano, trifluoromethyl, trifluoromethoxy, or a lower alkyl substituted with one of hydroxy, lower alkoxy, halo, cyano, trifluoromethyl, or trifluoromethoxy;

$R^{14}$ is selected from lower alkyl, hydroxy, lower alkoxy, halo, cyano, trifluoromethyl, trifluoromethoxy, and a lower alkyl substituted with one of hydroxy, lower alkoxy, halo, cyano, trifluoromethyl, or trifluoromethoxy;

m is 0 or 1; and n is 0 to 4; and prodrugs, individual isomers, mixtures of isomers, and pharmaceutically acceptable salts thereof.

The invention also relates to pharmaceutical compositions containing compounds of Formula (I), above, and methods of treating CCR-3 receptor mediated diseases, such as asthma, by administration of a therapeutically-effective amount of a compound of Formula (I), to a patient in need of treatment thereof.

DETAILED DESCRIPTION OF THE INVENTION

Definitions

Unless otherwise stated, the following terms used in the specification and claims have the meanings given below.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like. A "lower alkyl" is an alkyl group having one to four carbon atoms.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

When the term "alkyl" is used as a suffix following another term, as in "phenylalkyl," or "hydroxyalkyl," this is intended to refer to an alkyl group, as defined above, being substituted with at least one substituent selected from the other specifically named group. Thus, "phenylalkyl" would include, for example, benzyl and phenylethyl. "Hydroxyalkyl" includes, for example, 2-hydroxyethyl, 2-hydroxypropyl, 3-hydroxypropyl, 1-(hydroxymethyl)-2-methylpropyl, 2-hydroxybutyl, 2-hydroxy-1-hydroxymethylethyl, 2,3-dihydroxybutyl, 3,4-dihydroxybutyl and 2-(hydroxymethyl)-3-hydroxypropyl, and so forth. Accordingly, as used herein, the term "hydroxyalkyl" is used to define a subset of heteroalkyl groups defined below.

"Acyl" means a radical —C(=O)R, where R is hydrogen, alkyl, cycloalkyl, cycloalkylalkyl, phenyl or phenylalkyl wherein the alkyl, cycloalkyl, cycloalkylalkyl, and phenylalkyl groups are as defined herein. Representative examples include, but are not limited to formyl, acetyl, cyclohexylcarbonyl, cyclohexylmethylcarbonyl, benzoyl, benzylcarbonyl, and the like.

"Acylamino" means a radical —NR'C(=O)R, where R' is hydrogen or alkyl, and R is hydrogen, alkyl, cycloalkyl, cycloalkylalkyl, phenyl or phenylalkyl, wherein the alkyl, cycloalkyl, cycloalkylalkyl, and phenylalkyl groups are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R is an alkyl as defined herein e.g., methoxy, ethoxy, propoxy, butoxy and the like. A "lower alkoxy" is an alkoxy group wherein the alkyl (R) group has up to four carbon atoms.

"Alkoxycarbonyl" means a radical —C(=O)R where R is alkoxy is as defined herein.

"Alkylamino" or "Monoalkylamino" means a radical —NHR where R represents an alkyl, cycloalkyl or cycloalkyl-alkyl group as defined herein. Representative examples include, but are not limited to methylamino, ethylamino, isopropylamino, cyclohexylamino, and the like.

"Alkylene" means a linear saturated bivalent hydrocarbon radical of one to six carbon atoms or a branched saturated bivalent hydrocarbon radical of three to six carbon atoms, e.g., methylene, ethylene, 2,2-dimethylethylene, propylene, 2-methylpropylene, butylene, pentylene, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylsulfonyl" means a radical —S(O)$_2$R where R is an alkyl, cycloalkyl or cycloalkyl-alkyl group as defined herein, e.g., methylsulfonyl, ethylsulfonyl, propylsulfonyl, butylsulfonyl, cyclohexylsulfonyl and the like.

"Alkylsulfinyl" means a radical —S(O)R where R is an alkyl, cycloalkyl or cycloalkyl-alkyl group as defined herein e.g., methylsulfinyl, ethylsulfinyl, propylsulfinyl, butylsulfinyl, cyclohexylsulfinyl and the like.

"Alkylthio" means a radical —SR where R is an alkyl as defined above e.g., methylthio, ethylthio, propylthio, butylthio, and the like.

"Aryl" means a monocyclic or bicyclic aromatic hydrocarbon radical which is optionally substituted with one or more substituents, preferably one, two or three, substituents selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. Exemplary aryl groups include, but are not limited to, phenyl, chlorophenyl, fluorophenyl, methoxyphenyl, 1-naphthyl, 2-naphthyl, and the derivatives thereof.

"Cycloalkyl" refers to a saturated monovalent cyclic hydrocarbon radical of three to seven ring carbons e.g., cyclopropyl, cyclobutyl, cyclohexyl, 4-methylcyclohexyl, and the like.

"Dialkylamino" means a radical —NRR' where R and R' independently represent an alkyl, cycloalkyl, or cycloalkylalkyl group as defined herein. Representative examples include, but are not limited to dimethylamino, methylethylamino, di(1-methylethyl)-amino, (cyclohexyl)(methyl) amino, (cyclohexyl)(ethyl)amino, (cyclohexyl)(propyl) amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that when the heteroaryl group is a bicyclic system in which one of the rings is carbocyclic and/or non-aromatic, the point of attachment to the heteroaryl group will be to the aromatic ring containing at least one heteroatom. The heteroaryl ring is optionally substituted independently with one or more substituents, preferably one or two substituents, selected from alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy, ethylenedioxy or optionally substituted phenyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, 5-(3,4-dimethoxyphenyl)-pyrimidin-2-yl, 5-(4-methoxyphenyl)-pyrimidin-2-yl, 5-(3,4-methylenedioxyphenyl)-pyrimidin-2-yl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl and derivatives thereof.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heterocyclyl" means a saturated or unsaturated non-aromatic cyclic radical of 3 to 8 ring atoms in which one or two ring atoms are heteroatoms selected from NR$^x$ {wherein each R$^x$ is independently hydrogen, alkyl, acyl, alkylsulfonyl, aminosulfonyl, (alkylamino)sulfonyl, (dialkylamino)sulfonyl, carbamoyl, (alkylamino)carbonyl, (dialkylamino)carbonyl, (carbamoyl)alkyl, (alkylamino)carbonylalkyl, or dialkylaminocarbonylalkyl}, O, or S(O)$_n$ (where n is an integer from 0 to 2), the remaining ring atoms being carbon atoms. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino, dialkylamino, aralkyl, —(X)$_n$—C(=O)R (where X is O or NR', n is 0 or 1, R is hydrogen, alkyl, haloalkyl, hydroxy, alkoxy, amino, monoalkylamino, dialkylamino or optionally substituted phenyl, and R' is hydrogen or alkyl), -alkylene-C(=O)R (where R is hydrogen, alkyl, haloalkyl, hydroxy, alkoxy, amino, monoalkylamino, dialkylamino or optionally substituted phenyl) or —S(O)$_n$R$^d$ (where n is an integer from 0 to 2, and R$^d$ is hydrogen (provided that n is 0), alkyl, haloalkyl, cycloalkyl, cycloalkylalkyl, amino, monoalkylamino, dialkylamino, or hydroxyalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, tetrahydrothiophenyl-S,S-dioxide, pyrrolinyl, imidazolinyl, and the derivatives thereof.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl group which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term includes, but is not limited to, phenyl, chlorophenyl, fluorophenyl, bromophenyl, methylphenyl, ethylphenyl, methoxyphenyl, cyanophenyl, 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-methylphenyl, 3-chloro-4-fluorophenyl or 3,4-dichlorophenyl and the derivatives thereof.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

"Substituted alkyl" means an alkyl group having one or more, preferably one, two or three substituents selected from the group consisting of acyl, acylamino, hydroxy, alkoxy, amino, haloalkyl, halo, alkoxycarbonyl, alkylamino, alkylsulfonyl, alkylsulfinyl, alkylthio, aryl, cycloalkyl, dialkylamino, heteroaryl and/or heterocyclyl, as defined above.

"Pharmaceutically acceptable excipient" means an excipient that is useful in preparing a pharmaceutical composition that is generally safe, non-toxic and neither biologically nor otherwise undesirable, and includes excipients that are acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "prodrug" of a compound of formula (I) herein refers to any compound which releases an active drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the compound of Formula I. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a grouping of atoms that when attached to a reactive group in a molecule masks, reduces or prevents that reactivity. Examples of protecting groups can be found in T. W. Green and P. G. Wuts, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilylethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R— and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

PREFERRED EMBODIMENTS

While the broadest definition of this invention is set forth in the Summary of the Invention, certain compounds of Formula (I) are preferred.

Preferred compounds of the invention are compounds having Formula (I):

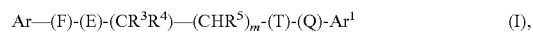

Ar—(F)-(E)-(CR$^3$R$^4$)—(CHR$^5$)$_m$-(T)-(Q)-Ar$^1$    (I), wherein:

T is

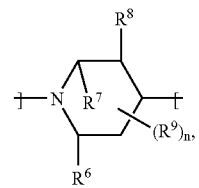

where R$^6$ is taken together with one of R$^7$ and R$^8$ to form a bridge of one to two bridgehead carbon atoms, and the other of R$^7$ and R$^8$ is selected from hydrogen and R$^9$;

Ar and Ar$^1$ are both phenyl;

F is a bond;

E is selected from —C(=O)N(R$^{10}$)—, —N(R$^{11}$)C(=O)N(R$^{10}$)—, —N(R$^{11}$)C(=O)—, —N(R$^{12}$)C(=O)CH(R$^{13}$)—, and CH(R$^{13}$)C(=O)N(R$^{12}$)—, where:

R$^{10}$, R$^{11}$, R$^{12}$, and R$^{13}$ are, independently of each other, hydrogen or alkyl;

or alternatively, R$^{12}$ and R$^{13}$ may be taken together with the nitrogen and carbon atoms to which they are attached, respectively, to form a heterocyclyl or heteroaryl ring optionally substituted with up to two groups selected from R$^{14}$;

R$^3$ and R$^4$ are, independently of each other, hydrogen, alkyl, or substituted alkyl (more preferably lower alkyl optionally substituted with hydroxy);

R$^5$ is hydrogen or alkyl;

Q is —C(=O)— or C$_{1-2}$alkylene;

$R^9$ is attached to any available carbon atom of ring T and is selected from lower alkyl, hydroxy, lower alkoxy, halo, cyano, trifluoromethyl, trifluoromethoxy, or a lower alkyl substituted with one of hydroxy, lower alkoxy, halo, cyano, trifluoromethyl, or trifluoromethoxy;

$R^{14}$ is selected from lower alkyl, hydroxy, lower alkoxy, halo, cyano, trifluoromethyl, trifluoromethoxy, and a lower alkyl substituted with one of hydroxy, lower alkoxy, halo, cyano, trifluoromethyl, or trifluoromethoxy;

m is 0 or 1; and n is 0 to 4; and prodrugs, individual isomers, mixtures of isomers, and pharmaceutically acceptable salts thereof.

Accordingly, in compounds of Formula (I), Ar and $Ar^1$ are preferably both phenyl, more preferably phenyl optionally substituted with one, two, or three groups selected from halo, alkyl, heteroalkyl, alkoxy, nitro, trifluoromethyl, and alkylsulfonyl. More preferably, Ar is selected from phenyl, 4-chlorophenyl, 4-methylphenyl, 4-methoxyphenyl, 3-methylsulfonylphenyl, 3,5-dimethoxyphenyl, 3,4-dimethoxyphenyl, and 3,4,5-trimethoxyphenyl, and $Ar^1$ is preferably selected from 4-chlorophenyl and 3,4-dichlorophenyl. Most preferred are compounds where Ar is 3,4,5-trimethoxyphenyl and $Ar^1$ is 4-chlorophenyl.

In compounds of Formula (I), F is preferably a bond and Q is $CH_2$—.

In compounds of formula (I), E is preferably selected from —C(=O)N($R^{10}$)—, —N($R^{11}$)C(=O)N($R^{10}$)—, and —N($R^{12}$)C(=O)CH($R^{13}$)—, where $R^{10}$, $R^{11}$, $R^{12}$, and $R^{13}$ are, independently of each other, hydrogen or alkyl; or alternatively, $R^{12}$ and $R^{13}$ may be taken together with the nitrogen and carbon atoms to which they are attached, respectively, to form

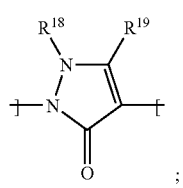

where $R^{18}$ and $R^{19}$ are selected from hydrogen and lower alkyl. In compounds of formula (I), preferably when E is

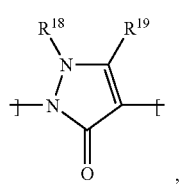

$R^{18}$ and $R^{19}$ are preferably methyl, and m is preferably 0. Most preferred are compounds where E is —NHC(=O)NH—.

In compounds of Formula (I), preferably T is selected from the group consisting of:

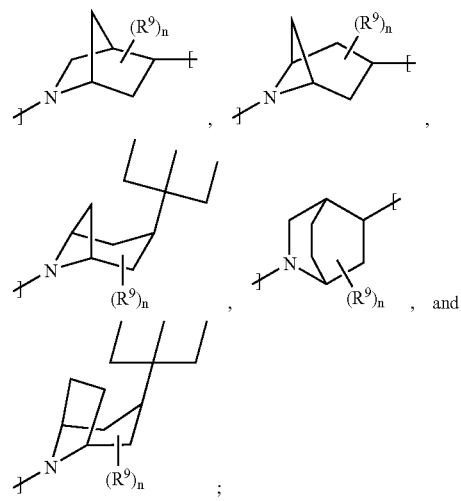

wherein $R^9$ is attached to any available carbon atom of ring T and is selected from lower alkyl and hydroxy, and n is 0 to 2. More preferably T is

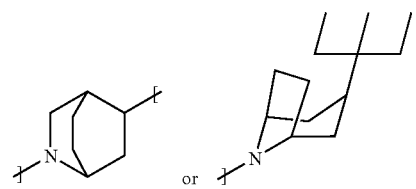

In compounds of Formula (I), preferably $R^3$ is hydrogen; and $R^4$ is hydrogen or optionally substituted lower alkyl; more preferably $R^3$ is hydrogen and $R^4$ is methyl, ethyl, 1-methylethyl, isopropyl, 1-hydroxyethyl or 2-hydroxyethyl. Further preferred compounds are those wherein $R^3$ is hydrogen; and $R^4$ is 1-methylethyl or 1-hydroxyethyl.

According to another aspect of the invention, preferred compounds are those compounds having the formula (II):

(II)

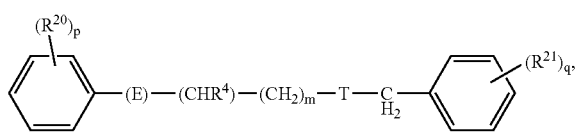

and pharmaceutically-acceptable salts thereof, in which:

T is

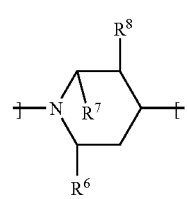

where $R^6$ is taken together with one of $R^7$ and $R^8$ to form a bridge of one to two bridgehead carbon atoms optionally substituted with one to two $CH_3$, and the other of $R^7$ and $R^8$ is selected from hydrogen and lower alkyl;

E is selected from —C(=O)N($R^{10}$)—, —N($R^{11}$)C(=O)N($R^{10}$)—, and —N($R^{12}$)C(=O)CH($R^{13}$)—, where:

$R^{10}$, $R^{11}$, $R^{12}$, and $R^{13}$ are independently of each other hydrogen or lower alkyl, or alternatively, $R^{12}$ and $R^{13}$ may be taken together with the nitrogen and carbon atoms to which they are attached, respectively, to form a five-membered heterocyclyl or heteroaryl ring having up to two N atoms and optionally substituted with up to two groups selected from methyl, ethyl, hydroxy, methoxy, halo, cyano, trifluoromethyl, and trifluoromethoxy;

$R^4$ is hydrogen, lower alkyl, or lower alkyl substituted with hydroxy;

$R^{20}$ and $R^{21}$ are each independently selected from halo, $OR^{22}$, and $SO_2R^{22}$, wherein $R^{22}$ is lower alkyl;

m is 0 or 1;

p and q are independently 0, 1, 2 or 3.

In compounds of formula (II), preferably E is selected from —C(=O)NH—, —NHC(=O)NH—, and

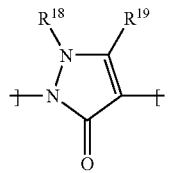

where $R^{18}$ and $R^{19}$ are each hydrogen or lower alkyl; preferably $R^4$ is hydrogen, methyl, ethyl, 1-hydroxyethyl, or 1-methylethyl; $R^{20}$ is selected from halo, methoxy, and methylsulfonyl; $R^{21}$ is halo (more preferably chloro); p is 0, 1, 2 or 3; and q is 0, 1, or 2.

More preferably, in compounds of formula (II), T is

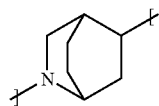

or

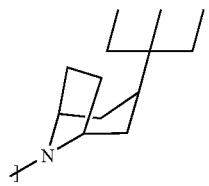

Further preferred compounds are those of Formula (II), above, wherein E and T are as immediately defined above; $R^{20}$ and the phenyl group to which each $R^{20}$ is attached together form phenyl, 3-methylsulfonylphenyl, 4-methylphenyl, or 3,4,5-trimethoxyphenyl, and $R^{21}$ and the phenyl group to which each $R^{21}$ is attached together form 4-chlorophenyl or 3,4-dichlorophenyl.

Utility

The compounds of the invention are CCR-3 receptor antagonists and inhibit eosinophil recruitment by CCR-3 chemokines such as RANTES, eotaxin, MCP-2, MCP-3 and MCP-4. Compounds of this invention and compositions containing them are useful in the treatment of eosiniphil-induced diseases such as inflammatory or allergic diseases and including respiratory allergic diseases such as asthma, allergic rhinitis, hypersensitivity lung diseases, hypersensitivity pneumonitis, eosinophilic pneumonias (e.g., chronic eosinophilic pneumonia); inflammatory bowel diseases (e.g., Crohn's disease and ulcerative colitis); and psoriasis and inflammatory dermatoses such as dermatitis and eczema.

Administration and Pharmaceutical Composition

In general, the compounds of this invention can be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.01–20 mg per kilogram body weight of the recipient per day; preferably about 0.1–10 mg/kg/day. Thus, for administration to a 70 kg person, the dosage range would most preferably be about 7 mg to 0.7 g per day.

In general, compounds of this invention will be administered as pharmaceutical compositions by any one of the following routes: oral, transdermal, inhalation (e.g., intranasal or oral inhalation) or parenteral (e.g., intramuscular, intravenous or subcutaneous) administration. A preferred manner of administration is oral using a convenient daily dosage regimen which can be adjusted according to the degree of affliction. Compositions can take the form of tablets, pills, capsules, semisolids, powders, sustained release formulations, solutions, suspensions, liposomes, elixirs, or any other appropriate compositions. Another preferred manner for administering compounds of this invention is inhalation. This is an effective means for delivering a therapeutic agent directly to the respiratory tract for the treatment of diseases such as asthma and other similar or related respiratory tract disorders (see U.S. Pat. No. 5,607,915).

The choice of formulation depends on various factors such as the mode of drug administration and the bioavailability of the drug substance. For delivery via inhalation the compound can be formulated as liquid solutions or suspensions, aerosol propellants or dry powder and loaded into a suitable dispenser for administration. There are three types of pharmaceutical inhalation devices-nebulizer inhalers, metered—dose inhalers (MDI) and dry powder inhalers (DPI). Nebulizer devices produce a stream of high velocity air that causes the therapeutic agents (which has been formulated in a liquid form) to spray as a mist which is carried into the patient's respiratory tract. MDI's typically have the formulation packaged with a compressed gas. Upon actuation, the device discharges a measured amount of therapeutic agent by compressed gas, thus affording a reliable method of administering a set amount of agent. DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

For liposomal formulations of the drug for parenteral or oral delivery the drug and the lipids are dissolved in a suitable organic solvent e.g. tert-butanol, cyclohexane (1% ethanol). The solution is lyophilized and the lipid mixture is suspended in an aqueous buffer and allowed to form a liposome. If necessary, the liposome size can be reduced by sonication. (See Frank Szoka, Jr. and Demetrios Papahadjopoulos, "Comparative Properties and Methods of Preparation of Lipid Vesicles (Liposomes)", *Ann. Rev. Biophys. Bioeng.*, 9:467–508 (1980), and D. D. Lasic, "Novel Applications of Liposomes", *Trends in Biotech.*, 16:467–608, (1998)).

Other suitable pharmaceutical excipients and their formulations are described in Remington's Pharmaceutical Sciences, edited by E. W. Martin (Mack Publishing Co., 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described below.

Testing

The CCR-3 antagonistic activity of the compounds of this invention can be measured by in vitro assays such as ligand binding and chemotaxis assays as described in more detail below. In vivo activity can be assayed in the Ovalbumin induced Asthma in Balb/c Mice Model as described in more detail below.

Abbreviations

For ease of reference, the following abbreviations are used in the Schemes and Examples below:

MeOH=methanol

EtOH=ethanol

EtOAc=ethyl acetate

HOAc=acetic acid

DCE=1,2-dichloroethane

DMF=dimethylformamide

PCC=pyridinium chlorochromate

PDC=pyridinium dichromate

TEA or $Et_3N$=triethylamine

THF=tetrahydrofuran

TFA=trifluoroacetic acid rt=room temperature

General Synthetic Schemes

The compounds of the present invention can be prepared in a number of ways known to one skilled in the art. Preferred methods include, but are not limited to, the general synthetic procedures described below.

The starting materials and reagents used are either available from commercial suppliers such as Aldrich Chemical Co. (Milwaukee, Wis., USA), Bachem (Torrance, Calif., USA), Enika Chemie or Sigma (St. Louis, Mo., USA), Maybridge (Dist: Ryan Scientific, P.O. Box 6496, Columbia, S.C. 92960), etc.; or are prepared by methods known to those skilled in the art following procedures set forth in the literature such as Fieser and Fieser's Reagents for Organic Synthesis, Volumes 1–17 (John Wiley and Sons, 1991); Rodd's Chemistry of Carbon Compounds, Volumes 1–5 and Supplements (Elsevier Science Publishers, 1989), Organic Reactions, Volumes 1–40 (John Wiley and Sons, 1991), March's Advanced Organic Chemistry, (John Wiley and Sons, 1992), and Larock's Comprehensive Organic Transformations (VCH Publishers Inc., 1989). These schemes are merely illustrative and various modifications to these schemes can be made and will be suggested to one skilled in the art having referred to this disclosure.

The starting materials and the intermediates of the reaction may be isolated and purified if desired using conventional techniques, including but not limited to, filtration, distillation, crystallization, chromatography, and the like. Such materials may be characterized using conventional means, including physical constants and spectral data. In the Schemes, the variables E, Q, Ar, Ar$^1$, R$^4$, R$^{20}$, R$^{21}$, p, q, etc., are defined as set forth in the claims.

General Scheme 1:

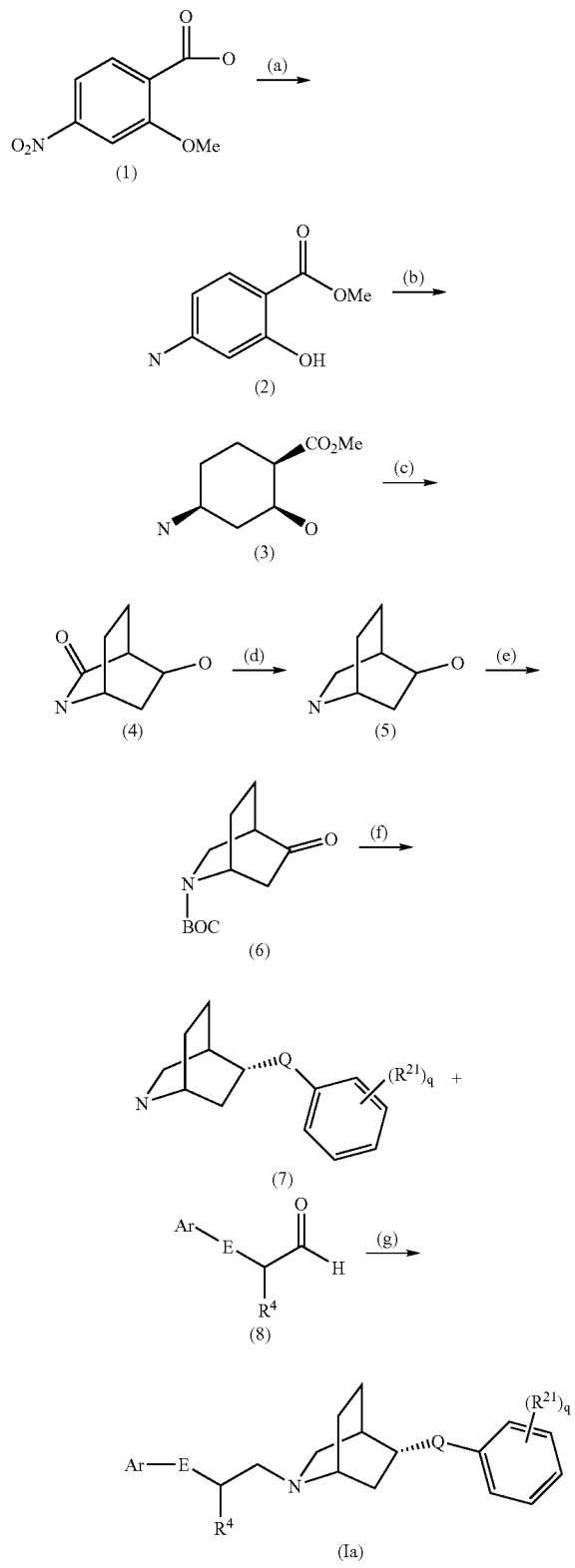

Step (a):

2-Methoxy-4-nitrobenzoic acid (1) in CH$_2$Cl$_2$ (97%) is reacted with BBr$_3$ to provide the intermediate 2-hydroxy-4-nitro-benzoic acid, which upon treatment with SOCl$_2$ in solvent such as MeOH (95%), followed by hydrogenation and treatment with 10% Pd/C in EtOAc (98%) yields 4-amino-2-hydroxy-benzoic acid methyl ester (2).

Step (b):

Hydrogenation of methyl ester (2) [e.g., 53 psi, 5% Rh on Al in acetic acid (70 h), 58° C.] affords 4-amino-2-hydroxy-cyclohexanecarboxylic acid methyl ester (3) as the acetic acid salt.

Step (c):

Reaction of compound (3) with mesitylene at elevated temperature (e.g., 165° C.) followed by cooling to rt yields 5-hydroxy-2-aza-bicyclo[2.2.2]octan-3-one (4).

Step (d):

Compound (4) can be reacted with LAH in solvent (such as THF), with reflux under nitrogen to yield 2-aza-bicyclo[2.2.2]octane-5-ol (5).

Step (e):

Compound (5) can be N-Boc protected upon mixing with (Boc)$_2$O (86%) in an appropriate solvent (e.g., MeOH, TEA). N-Boc protected compound (5) can be converted to N-Boc protected 2-aza-bicyclo[2.2.2]octan-5-one (6) upon treatment with PDC in an appropriate solvent such as CH$_2$Cl$_2$ (96%) or DMF.

Step (f):

N-Boc protected 2-aza-bicyclo[2.2.2]octan-5-one (6) can be converted to the appropriately-substituted compound (7) via addition of 3,4-di-ClPhCH$_2$P(O)(OEt)$_2$ in solvent such as THF at reduced temperature (e.g., 0° C.), followed by hydrogenation in solvent (such as EtOH:EtOAc or EtOAc), in the presence of PtO$_2$ (88%) and addition of TFA (99%).

Step (g):

Bicyclo-octane (7) can be reacted with an appropriately-substituted aldehyde (8) in solvent such as CH$_2$Cl$_2$ (36%) or DCE upon addition of Me$_4$NB(OAc)$_3$H or NaBH(OAc)$_3$, to yield compounds having the formula (Ia).

General Scheme 2:

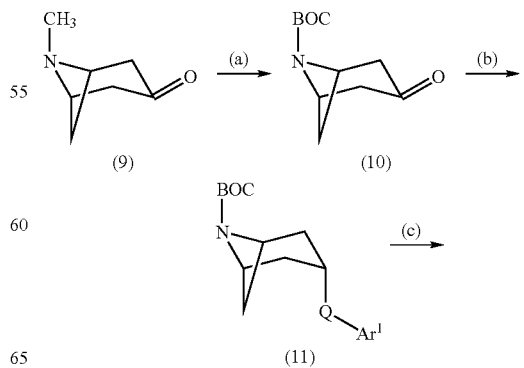

17

-continued

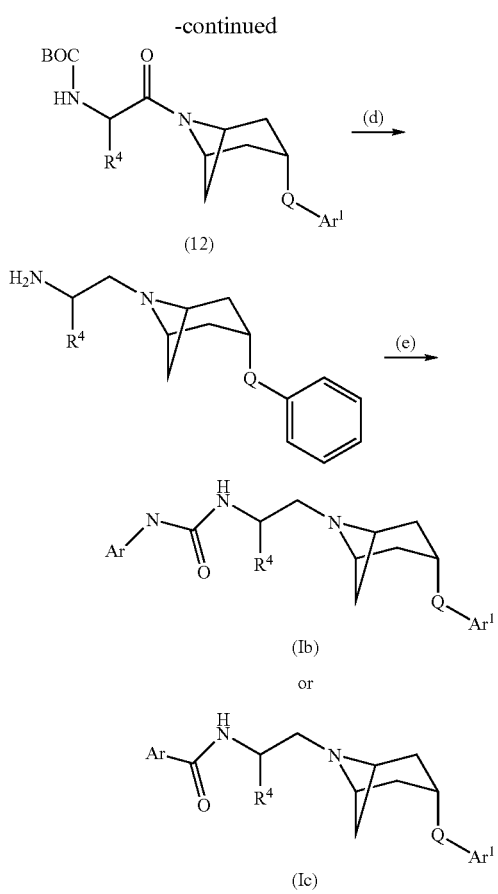

Step (a):
8-Methyl-8-aza-bicyclo[3.2.1]octan-3-one can be treated with 1-Cl-ethyl chloroformate in an appropriate solvent such as MeOH (88%) or DCE, followed by addition of (Boc)₂O (98%) to afford compound (10).

Step (b):
Compound (10) can be treated with an appropriate phosphonic acid diethyl ester [e.g., Ar¹-Q-P(O)(MeO)₂], in the presence of base (e.g., potassium t-amylate or NaH), and then hydrogenated in the presence of PtO₂ under H₂ and extracted with EtOAc to afford compound (11).

Steps (c)–(d):
Compound (11) can be treated with TFA in an appropriate solvent such as CH₂Cl₂, then reacted with (Boc)NHCH(R⁴)CO₂H, EDCl and/or HOBT in CH₂Cl₂, then reacted with TFA and refluxed with BH₃-THF at elevated temperature, followed by cooling and addietion of HCl (aq.) to provide compound (13).

Step (e):
Compound (13) can be treated with 4-toluoyl chloride and Et₃N in CH₂Cl₂ or reacted with an appropriately-substituted isocyanate to afford compounds of formulae (Ib) and/or (Ic).

The following Examples are provided as additional guidance for those of skill in the art, and are not intended to limit the invention in any way.

18

EXAMPLE 1

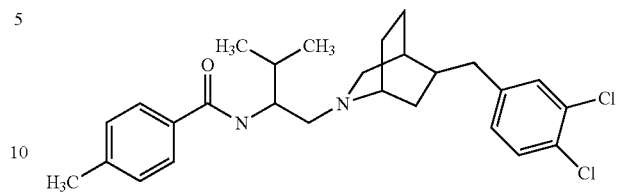

Step 1:
To a solution of 2-methoxy-4-nitro-benzoic acid (20 g, 0.102 mol) in 80 ml of CH₂Cl₂ at 0° C. was added BBr₃ (1.0 M, 150 ml, 1.5 eq.). The resulting mixture was allowed to warm to rt and stirred for 2 h. MeOH was then added dropwise to quench the reaction at 0° C. and the volatile fraction was removed in vacuo. The residue was purified on a silica gel column with 6/4/0.3 of hexane, EtOAc and HOAc to give 18 g of 2-hydroxy-4-nitro-benzoic acid (M⁺: 183).

Step 2:
To a MeOH solution (200 ml) of 2-hydroxy-4-nitro-benzoic acid (18 g) was added concentrated sulfuric acid. The resulting mixture was heated to reflux for 24 h. After it was cooled to rt, volatile was removed in vacuo. The residue was then partitioned between water and EtOAc. The EtOAc layer was washed with water (2×), NaHCO₃ (sat.), NaCl (sat.), dried over Na₂SO₄ and concentrated. The crude product was purified on a silica gel column with 20% EtOAc in hexane to give 14.5 g of 2-hydroxy-4-nitro-benzoic acid methyl ester as a solid (M⁺: 197).

Step 3:
2-Hydroxy-4-nitro-benzoic acid methyl ester (14 g) was dissolved in EtOH (100 ml) and THF (10 ml) and stirred under hydrogen (1 atm) in the presence of PtO₂ for 24 h. The reaction mixture was then filtered through a celite bed. The filtrate was concentrated to give 12 g of 4-Amino-2-hydroxy-benzoic acid methyl ester as a light yellow solid.

Step 4:
4-Amino-2-hydroxy-benzoic acid methyl ester (10 g) in 200 ml of HOAc was hydrogenated under 56 psi pressure at 60° C. for 42 h. The volatile was then removed. The residue was stirred in 50 ml of 4/1 of ether/EtOH and precipitate formed. Filtration gave 6.5 g of 4-amino-2-hydroxy-cyclohexanecarboxylic acid methyl ester acetic acid salt (m.p. 125.5–126.4° C.; M⁺: 173).

Step 5:
4-Amino-2-hydroxy-cyclohexanecarboxylic acid methyl ester acetic acid salt (6.6 g) was heated to reflux in mesitylene (60 ml) for 3 h. After cooling to rt, solvent was decanted and the crystals were washed with hexane three times to provide 2.9 g of 5-hydroxy-2-aza-bicyclo[2.2.2]octan-3-one (M⁺: 141).

Step 6:
To a solution of 5-hydroxy-2-aza-bicyclo[2.2.2]octan-3-one (2.6 g, 18 mmol) in 60 ml of anhydrous THF was added 55 ml of LAH (1.0 M in THF). After the mixture was refluxed under N₂ for 24 h, it was cooled to rt and quenched with 2 ml of water, followed by 2 ml of 15% NaOH and 6 ml of water. The suspension was then stirred with MgSO₄ and filtered. The filtrate was acidified with 1.0 M of HCl in ether and then concentrated to afford 3.2 g of 2-aza-bicyclo[2.2.2]octan-5-ol as the HCl salt.

Step 7:

2-Aza-bicyclo[2.2.2]octan-5-ol (3.2 g, 0.02 mol) was mixed with di-t-butyl dicarbonate (8.8 g, 2 eq.) in 60 ml of EtOH and 7.6 ml of TEA (3 eq.) and the resulting mixture was heated under $N_2$ at 60° C. for 3 h. The volatile fraction was removed and the residue was partitioned between EtOAc and water. The organic layer was washed with saturated NaCl (aq.) and dried over $Na_2SO_4$ to afford N-Boc protected 2-aza-bicyclo[2.2.2]octan-5-ol (3 g)($M^+$: 227).

Step 8:

To a solution of N-Boc protected 2-aza-bicyclo[2.2.2]octan-5-ol (3.0 g, 31.4 mmol) in DMF at 0° C. was added 30 g of PDC (7 eq.). The resulting mixture was stirred for 6 h and filtered through a celite bed. The filtrate was concentrated and purified on a silica gel column with 20% EtOAc in hexane to give 1.74 g of N-Boc protected 2-aza-bicyclo[2.2.2]octan-5-one ($M^+$: 225).

Step 9:

Triethylphosphite (4.28 ml) was added dropwise to 3,4-dichlorobenzylbromide (6.0 g, 25 mmol) at rt with stirring. After 1 ml of triethylphosphite was added, the mixture was heated to 80° C. until an exothermic reaction was started. The remaining phosphite was added at a rate sufficient to maintain the reflux. After the addition was completed, the mixture was heated to reflux for 1 h and allowed to cool. The crude product was distilled under vacuum at 155–158° C./1–2 torr to afford (3,4-dichlorobenzyl)-phosphonic acid diethyl ester (6.5 g).

Step 10:

To a suspension of NaH (53 mg, 2.1 mmol) in 8 ml of THF with 13 mg of 15-crown-5 (3%) was added N-Boc protected 2-aza-bicyclo[2.2.2]octan-5-one (0.45 g, 2 mmol) (from Step 8) and (3,4-Dichloro-benzyl)-phosphonic acid diethyl ester (0.594, 2 mmol) (from Step 9) in 4 ml of THF dropwise at 0° C. under $N_2$. Hydrogen evolution was observed and the solution turned yellow. After the completion of the addition, the mixture was stirred at 0° C. for 1 h and at rt for 2 h. It was then quenched with water and extracted with EtOAc. The EtOAc layer was washed with NaCl (sat.), dried over $Na_2SO_4$ and concentrated. Purification on a silica gel column with 20% EtOAc in hexane gave 0.45 g of 5-(3,4-dichlorobenzylidene)-2-aza-bicyclo[2.2.2]octane-2-carboxylic acid tert-butyl ester ($M^+$: 367).

Step 11:

5-(3,4-Dichloro-benzylidene)-2-aza-bicyclo[2.2.2]octane-2-carboxylic acid tert-butyl ester (0.45 g) was stirred under 1 atm of $H_2$ in 20 ml of 1:1 of EtOH:EtOAc in the presence of $PtO_2$ for 20 min. The reaction mixture was filtered through celite and concentrated to give 0.4 g of 5-(3,4-dichloro-benzyl)-2-aza-bicyclo[2.2.2]octane-2-carboxylic acid tert-butyl ester ($M^+$: 369).

Step 12:

To a solution of 5-(3,4-dichloro-benzyl)-2-aza-bicyclo[2.2.2]octane-2-carboxylic acid tert-butyl ester (0.24 g, 0.65 mmol) in 2 mL of $CH_2Cl_2$ was added 1 mL of TFA. After the mixture was stirred at rt for 1 h, it was quenched with $NaHCO_3$ (sat.). It was then extracted with $CH_2Cl_2$ and the organic layer was washed with NaCl (sat.), dried over $Na_2SO_4$ and concentrated to give 170 mg of 5-(3,4-Dichloro-benzyl)-2-aza-bicyclo[2.2.2]octane ($M^++1$: 270).

Step 13:

To a solution of valinol (DL, 5.0 g, 0.048 mol) in 200 mL of $CH_2Cl_2$ in the presence of $Et_3N$ (18.4 mL, 3eq.) at 0° C. was added 4-methyl-benzoyl chloride (7.1 mL, 1.1 eq.) in 50 mL of $CH_2Cl_2$ dropwise. After the addition was complete, the mixture was stirred at rt overnight. It was then quenched with water, and the organic layer was extracted with $CH_2Cl_2$, washed with NaCl (sat.), dried over $Na_2SO_4$ and concentrated. Column purification with 2/2/6 of acetone/$CH_2Cl_2$/hexane gave 7.8 g of white solid N-(1-hydroxymethyl-2-methyl-propyl)-4-methyl-benzamide ($M^+$: 221).

Step 14:

To a suspension of PCC in 20 mL of $CH_2Cl_2$ was added N-(1-hydroxymethyl-2-methyl-propyl)-4-methyl-benzamide (2.2 g, 10 mmol) in 15 mL of $CH_2Cl_2$. After the mixture was stirred for 1.5 h, it was diluted with $Et_2O$ and filtered through a celite bed. The filtrate was concentrated and the residue purified on a silica gel column with 20% EtOAc in hexane to give 0.75 g of N-(1-formyl-2-methyl-propyl)-4-methyl-benzamide as a white solid ($M^++1$: 220).

Step 15:

To a solution of N-(1-formyl-2-methyl-propyl)-4-methyl-benzamide (0.083 g, 1.2 eq.) and 5-(3,4-dichloro-benzyl)-2-aza-bicyclo[2.2.2]octane (0.085 g, 0.32 mmol) in 2 mL of $CH_2Cl_2$ at rt was added $NaBH(OAc)_3$ (96 mg, 1.1 eq.). After the resulting mixture was stirred for 16 h, it was quenched with $NaHCO_3$ (sat.) and extracted with EtOAc. The organic layer was washed with NaCl (sat.), dried over $Na_2SO_4$ and concentrated. Preparative TLC with 5% MeOH in $CH_2Cl_2$ and recrystallization from $CH_2Cl_2$ and hexane gave 50 mg of the compound of Example 1, N-(1-[5-(3,4-dichlorobenzyl)-2-aza-bicyclo[2.2.2]oct-2-ylmethyl]2-methylpropyl)-4-methylbenzamide, ($M^++1$: 473).

EXAMPLE 2

4-[5-(3,4-Dichloro-benzyl)-2-aza-bicyclo[2.2.2]oct-2-ylmethyl]-1,5-dimethyl-2-phenyl-1,2-dihydro-pyrazol-3-one

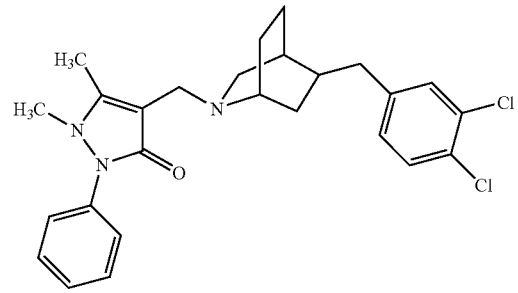

To a solution of 5-(3,4-dichloro-benzyl)-2-aza-bicyclo[2.2.2]octane (0.05 g, 0.35 mmol) in 2 ml of DCE was added 1,5-dimethyl-3-oxo-2-phenyl-2,3-dihydro-1H-pyrazole-4-carbaldehyde (90 mg, 1.2 eq.), and the mixture was stirred at rt for 15 min. $NaBH(OAc)_3$ (0.11 g, 1.5 eq.) was then added and the mixture was stirred at rt overnight, then with $NaHCO_3$ (sat.), and extracted with EtOAc. The EtOAc layer was washed with NaCl (sat.), dried over $Na_2SO_4$ and concentrated. Preparative TLC with 10% (10% $NH_4OH$ in MeOH) in $CH_2Cl_2$ gave 82 mg of Example 2 ($M^++1$: 470).

EXAMPLE 3

N-{1-[3-(3,4-Dichloro-benzyl)-8-aza-bicyclo[3.2.1]oct-8-ylmethyl]-2-methyl-propyl}-4-methyl-benzamide

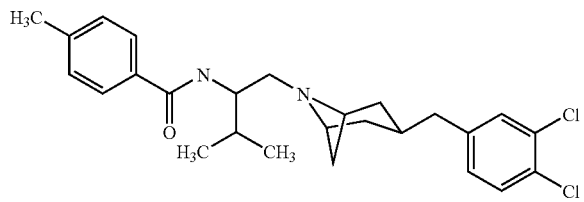

Step 1:

To a solution of 8-methyl-8-aza-bicyclo[3.2.1]octan-3-one (6.8 g, 0.05 mol) in 80 mL of DCE was added 1-chloroethyl chloroformate (8 mL, 1.5 eq.) dropwise at 0° C. After the addition was complete, the reaction mixture was allowed to warm to rt and was then heated to reflux for 3 h. After volatile was removed, the solid residue was dissolved in 100 mL of MeOH and then heated to reflux for 45 min. The volatile fraction was then removed again in vacuo and 8-aza-bicyclo[3.2.1]octan-3-one hydrochloride was recrystallized from MeOH/Et$_2$O as a solid product (58% yield) (4.58 g).

Step 2:

To a solution of 8-aza-bicyclo[3.2.1]octan-3-one hydrochloride (4.5 g, 0.028 mol) in 100 mL of EtOH was added carbonic acid di-tert-butyl ester (12 g, 2 eq.) and 11 mL of TEA. The resulting mixture was heated at 60° C. for 3 h. The volatile fraction was removed and the residue was partitioned between EtOAc and water. The EtOAc layer was washed with saturated sodium chloride, dried over Na$_2$SO$_4$ and concentrated. Silica gel column purification with 20% EtOAc in hexane gave 3-oxo-8-aza-bicyclo[3.2.1]octane-8-carboxylic acid tert-butyl ester (6.25 g).

Step 3:

To a suspension of NaH (0.24 g, 1.2 eq.) and 15-crown-5 (88 mg, 5%) in 32 mL of THF at 0° C. was added a solution of 3-oxo-8-aza-bicyclo[3.2.1]octane-8-carboxylic acid tert-butyl ester (1.8 g, 8 mmol) and (3,4-dichloro-benzyl)-phosphonic acid diethyl ester (2.6 g, 8.8 mmol) in 16 mL of THF. The resulting mixture was stirred at 0° C. for 1 h and at rt for 5 h. It was then quenched with H$_2$O and extracted with EtOAc. The organic layer was separated, washed with NaCl (sat.) and dried over Na$_2$SO$_4$. Column purification with 20% EtOAc in hexane provided 1.2 g of the starting material (3-Oxo-8-aza-bicyclo[3.2.1]octane-8-carboxylic acid tert-butyl ester) and 1 g of the desired product, 3-(3,4-dichloro-benzylidene)-8-aza-bicyclo[3.2.1]octane-8-carboxylic acid tert-butyl ester (M$^+$+1: 368).

Step 4:

3-(3,4-Dichloro-benzylidene)-8-aza-bicyclo[3.2.1]octane-8-carboxylic acid tert-butyl ester (1.0 g, 2.7 mmol) in 10 mL of EtOH and 10 mL of EtOAc was stirred with 25 mg of PtO$_2$ under 1 atm of H$_2$ at rt for 3 h. It was then filtered through a celite bed and the filtrate was concentrated. The residue was purified on a silica gel column to give 0.84 g of 3-(3,4-dichloro-benzyl)-8-aza-bicyclo[3.2.1]octane-8-carboxylic acid tert-butyl ester (M$^+$+1: 370).

Step 5:

3-(3,4-Dichloro-benzyl)-8-aza-bicyclo[3.2.1]octane-8-carboxylic acid tert-butyl ester (0.35 g, 0.94 mmol) was stirred in 2 mL of CH$_2$Cl$_2$ with 0.5 mL of TFA at rt for 3 h. After being quenched with 20% NaOH to basic medium, the mixture was extracted with EtOAc. The organic layer was washed with NaCl (sat.), dried over Na$_2$SO$_4$ and concentrated to give 0.25 g of 3-(3,4-Dichloro-benzyl)-8-aza-bicyclo[3.2.1]octane.

Step 6:

To a solution of N-(1-formyl-2-methyl-propyl)-4-methyl-benzamide (0.11 g, 0.44 mmol) (prepared according to example 1, step 13 and 14) and 3-(3,4-dichloro-benzyl)-8-aza-bicyclo[3.2.1]octane (0.11 g, 0.4 mmol) in 2 mL of CH$_2$Cl$_2$ at rt was added NaBH(OAc)$_3$. After the resulting mixture was stirred for 12 h, it was quenched with NaHCO$_3$ (sat.) and extracted with EtOAc. The organic layer was washed with NaCl (sat.), dried over Na$_2$SO$_4$ and concentrated. Preparative TLC with 5% (10% NH$_4$OH in MeOH) in CH$_2$Cl$_2$ and acidification with HCl gave 125 mg of Example 3 (m.p. 230–235° C.; M$^+$+1: 473)

EXAMPLE 4

(R)-1-{2-[4-(4-Chloro-benzyl)-2-ethyl-6-methyl-piperidin-1-yl]-1-methyl-ethyl}-3-(3,4,5-trimethoxy-phenyl)-urea

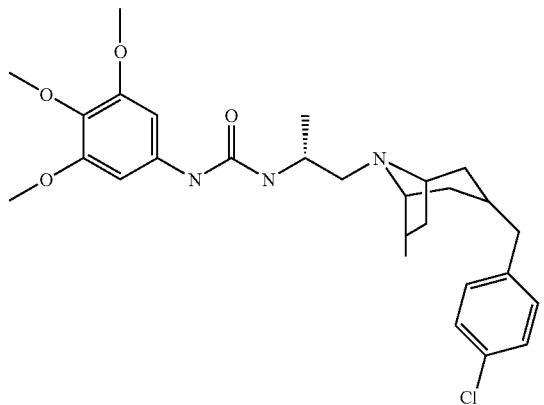

Step 1:

To a stirred solution of trimethylphosphite (0.57 ml, 4.9 mmol) was added 4-chlorobenzylbromide (1.0 g, 4.9 mmol) at rt. The resulting mixture was stirred at rt for 5 min. and then heated in an oil bath at 80° C. for 20 min. It was cooled to rt and the product purified on a silica-gel column with 25% EtOAc in hexane to give 1.05 g of (4-chloro-benzyl)-phosphonic acid dimethyl ester (93%).

Step 2:

3-(4-Chloro-benzylidene)-8-aza-bicyclo[3.2.1]octane-8-carboxylic acid tert-butyl ester was prepared according to the procedure described in example 3, step 3, but substituting (3,4-dichloro-benzyl)-phosphonic acid diethyl ester for (4-chloro-benzyl)-phosphonic acid dimethyl ester. Hydrogenation of 3-(4-chloro-benzylidene)-8-aza-bicyclo[3.2.1]octane-8-carboxylic acid tert-butyl ester under atmospheric hydrogen in the presence of PtO$_2$ in EtOH gave 3-(4-chloro-benzyl)-8-aza-bicyclo[3.2.1]octane-8-carboxylic acid tert-butyl ester in 65% yield (M$^+$: 335).

Step 3:

3-(4-chloro-benzyl)-8-aza-bicyclo[3.2.1]octane-8-carboxylic acid tert-butyl ester (0.88 g, 2.6 mmol) was stirred in 10 mL of CH$_2$Cl$_2$ with 10 mL of TFA at rt for 45 min. After it was quenched with 20% NaOH to basic medium, the mixture was extracted with EtOAc. The organic layer was washed with NaCl (sat.), dried over Na$_2$SO$_4$ and concentrated to give 0.52 g of 3-(4-Dichloro-benzyl)-8-aza-bicyclo [3.2.1]octane (85%).

Step 4:

A mixture of 3-(4-Dichloro-benzyl)-8-aza-bicyclo[3.2.1] octane, (D)-2-t-butoxy-carbonylamino-propionic acid, HOBT and EDCl in CH$_2$Cl$_2$ was stirred at rt overnight. It was then quenched with Na$_2$CO$_3$ (sat.) and extracted with CH$_2$Cl$_2$. The organic layer was washed with NaCl (sat.) and dried over Na$_2$SO$_4$. The crude product ({2-[3-(4-chloro-benzyl)-8-aza-bicyclo[3.2.1]oct-8-yl]-1-methyl-2-oxo-ethyl}carbamic acid tert-butyl ester) was purified on a silica-gel column with 25% acetone in CH$_2$Cl$_2$. It was then reacted with TFA in CH$_2$Cl$_2$ at rt for 2 h. The work-up procedure described in step 3, above, gave the desired product, which was dissolved in THF and heated to reflux with BH$_3$-THF for 4 h. After cooling to rt, the reaction flask was further cooled to 0° C. and 6N HCl was added. The resulting mixture was heated again to reflux for 1 h, cooled to rt and quenched with Na$_2$CO$_3$ (sat.). The mixture was extracted with EtOAc and the organic layer was washed with NaCl (sat.) and dried over Na$_2$SO$_4$. The crude product was purified on a silica-gel with 40% EtOAc in hexane and followed by 1% iPr-NH$_2$, 9% MeOH in EtOAc to give 2-[3-(4-chlorobenzyl)-8-aza-bicyclo[3.2.1]oct-8-yl]-1-methyl-ethylamine in 55% yield.

Step 5:

To a solution of 2-[3-(4-chlorobenzyl)-8-aza-bicyclo [3.2.1]oct-8-yl]-1-methyl-ethylamine in CH$_2$Cl$_2$ was added 3,4,5-trimethoxyphenylisocyanate at −78° C. After the addition, it was allowed to warm up to rt where it was stirred for 4 h. It was then diluted with CH$_2$Cl$_2$. The organic layer was washed with NaCl (sat.) and dried over Na$_2$SO$_4$. The crude product was purified on a silica-gel column with 3% (10% iPr-NH$_2$ in MeOH) in EtOAc to give 55% of Example 4 (m.p. 115–120° C., M$^+$: 502).

EXAMPLE 5

1-{2-[4-(4-Chloro-benzyl)-2-ethyl-6-methyl-piperidin-1-yl]-1-methyl-ethyl}-3-(3-methanesulfonylphenyl)urea

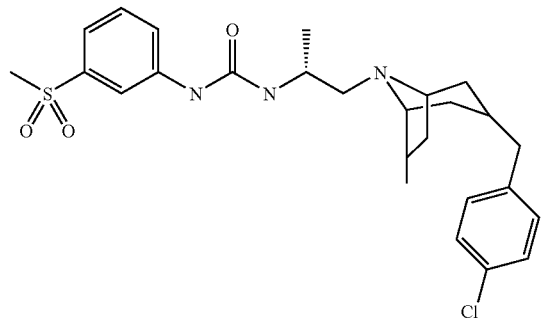

To a solution of triphosgene (0.22 g, 0.33 eq.) in CH$_2$Cl$_2$ was added 3-methane-sulfonyl-phenylamine hydrochloride (0.5 g, 2.4 mmol), followed by the dropwise addition of TEA (0.37 ml, 1.1 eq.). The mixture was heated to 40° C. for 30 min. It was allowed to cool to rt and stirred for an additional 45 min. The isocyanate solution was then added to a solution of 2-[3-(4-chlorobenzyl)-8-aza-bicyclo[3.2.1]oct-8-yl]-1-methyl-ethylamine (0.18 g, 0.6 mmol) (prepared according to the procedure described in example 4, steps 1 to 4) in 6 ml of CH$_2$Cl$_2$. The mixture was stirred overnight at rt. It was diluted with CH$_2$Cl$_2$ and the organic layer was washed with Na$_2$CO$_3$ (sat.) twice, NaCl (sat.) and dried over Na$_2$SO$_4$. The crude mixture was purified on a silica-gel column with 1% iPrNH$_2$, 9% MeOH in EtOAc to give 55% of Example 5 (M$^+$: 490).

EXAMPLES 6–10

Compounds described below in Table 1 were prepared following the same or similar methods described above for Examples 1–5.

TABLE 1

| Ex. No. | Structure | Compound Name | Data |
|---|---|---|---|
| 6 | 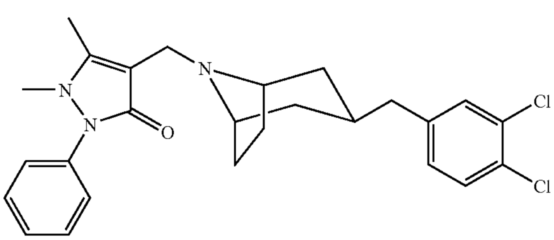 | 4-[3-(3,4-dichloro-benzyl)-8-aza-bicyclo[3.2.1]oct-8-ylmethyl]-1,5-dimethyl-2-phenyl-1,2-dihydro-pyrazol-3-one | M$^+$ + 1: 470 |

TABLE 1-continued

| Ex. No. | Structure | Compound Name | Data |
|---|---|---|---|
| 7 | 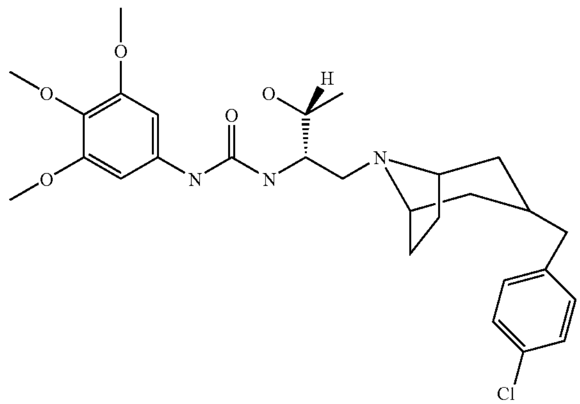 | 1-{1-[4-(4-Chloro-benzyl)-2-ethyl-6-methyl-piperidin-1-yl-methyl]-2-hydroxy-propyl}-3-(3,4,5-tri-methoxyphenyl)-urea | m.p. 118–123° C.; M+: 532 |
| 8 | 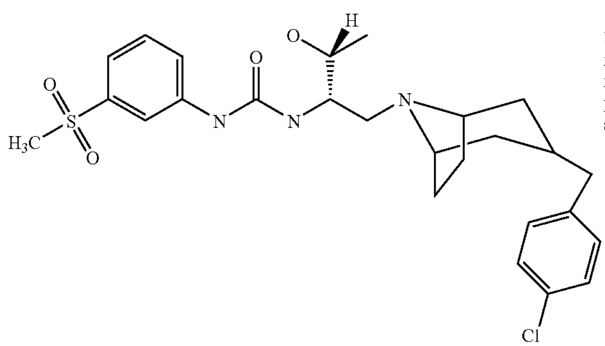 | 1-{1-[4-(4-Chloro-benzyl)-2-ethyl-6-methyl-piperidin-1-yl-methyl]-2-hydroxy-propyl}-3-(3-methane-sulfonyl-phenyl)-urea | m.p. 94–103° C.; M+: 520 |
| 9 | 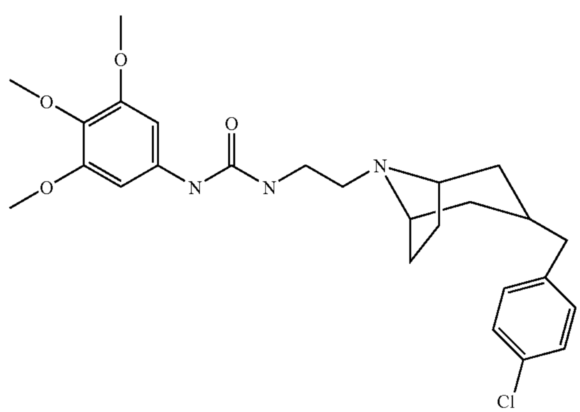 | 1-{2-[4-(4-chloro-benzyl)-2-ethyl-6-methyl-piperidin-1-yl]-ethyl}-3-(3,4,5-trimeth-oxy-phenyl)-urea | m.p. 107–111° C.; M+: 488. |
| 10 | 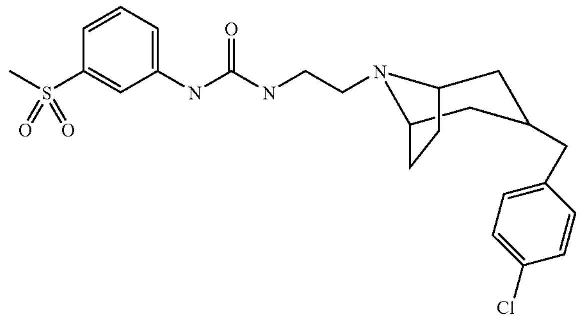 | 1-{2-[4-(4-Chloro-benzyl)-2-ethyl-6-methyl-piperidin-1-yl]-ethyl}-3-(3-methane-sulfonyl-phenyl)-urea | M+: 476. |

EXAMPLE 11

Formulation Examples

The following are representative pharmaceutical formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbit (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

Liposomal Formulation

The following ingredients are mixed to form a liposomal formulation.

| Ingredient | Amount |
|---|---|
| compound of this invention | 10 mg |
| L-.alpha.-phosphatidylcholine | 150 mg |
| tert-butanol | 4 ml |

Freeze dry the sample and lyophylize overnight. Reconstitute the sample with 1 ml 0.9% saline solution. Liposome size can be reduced by sonication.

EXAMPLE 12

CCR-3 Receptor Binding Assay—In Vitro

The CCR-3 antagonistic activity of the compounds of the invention was determined by their ability to inhibit the binding of $^{125}$I eotaxin to CCR-3 L1.2 transfectant cells (see Ponath, P. D. et al., *J. Exp. Med.*, 183:2437–48, (1996)).

The assay was performed in Costar 96-well polypropylene round bottom plates. Test compounds were dissolved in DMSO and then diluted with binding buffer (50 mM HEPES, 1 mM $CaCl_2$, 5 mM $MgCl_2$, 0.5% bovine serum albumin (BSA), 0.02% sodium azide, pH 7.24) such that the final DMSO concentration was 2%. 25 µl of the test solution or only buffer with DMSO (control samples) was added to each well, followed by the addition of 25 µl of $^{125}$I-eotaxin (100 pmol) (NEX314, New England Nuclear, Boston, Mass.) and $1.5 \times 10^5$ of the CCR-3 L1.2 transfected cells in 25 µl binding buffer. The final reaction volume was 75 µl.

After incubating the reaction mixture for 1 hour at rt, the reaction was terminated by filtering the reaction mixture through a polyethylenimine-treated Packard Unifilter GF/C filter plate (Packard, Chicago, Ill.). The filters were washed four times with ice cold wash buffer containing 10 mm HEPES and 0.5 M sodium chloride (pH 7.2) and dried at 65° C. for approximately 10 minutes. 25 µl/well of Microscint-20® scintillation fluid (Packard) was added and the radioactivity retained on the filters was determined by using the Packard TopCount®

Compounds of this invention were active in this assay. Representative $IC_{50}$ values (nM) obtained with this binding assay for certain compounds listed in Examples herein are shown below in Table 2.

TABLE 2

| Ex. No. | $IC_{50}$ (nM) |
|---|---|
| 2 | 331 |
| 4 | 11 |
| 6 | 965 |
| 7 | 8.2 |

EXAMPLE 13

Inhibition of Eotaxin Mediated Chemotaxis of CCR-3 L1.2 Transfectant Cells—In Vitro Assay The CCR-3 antagonistic activity of the compounds of this invention can be determined by measuring the inhibition of eotaxin mediated chemotaxis of the CCR-3 L1.2 transfectant cells, using a slight modification of the method described in Ponath, P. D. et al., *J. Clin. Invest.* 97:604–12 (1996). The assay is performed in a 24-well chemotaxis plate (Costar Corp., Cambridge, Mass.). CCR-3 L1.2 transfectant cells are grown in culture medium containing RPMI 1640, 10% Hyclone® fetal calf serum, 55 mM 2-mercaptoethanol and Geneticin 418 (0.8 mg/ml). 18–24 hours before the assay, the transfected cells are treated with n-butyric acid at a final concentration of 5 mM/,1×10⁶ cells/ml, isolated and resuspended at 1×10⁷ cells/ml in assay medium containing equal parts of RPMI 1640 and Medium 199 (M 199) with 0.5% bovine serum albumin.

Human eotaxin suspended in phosphate buffered saline at 1 mg/ml is added to bottom chamber in a final concentration of 100 nm. Transwell culture inserts (Costar Corp., Cambridge, Mass.) having 3 micron pore size are inserted into each well and L1.2 cells (1×10⁶) are added to the top chamber in a final volume of 100 µl. Test compounds in DMSO are added both to the top and bottom chambers such that the final DMSO concentration is 0.5%. The assay is performed against two sets of controls. The positive control contained cells with no test compound in the top chamber and only eotaxin in the lower chamber. The negative control contains cells with no test compound in the top chamber and neither eotaxin nor test compound in lower chamber. The plate is incubated at 37° C. After 4 hours, the inserts are removed from the chambers and the cells that have migrated to the bottom chamber are counted by pipetting out 500 µl of the cell suspension from the lower chamber to 1.2 ml Cluster tubes (Costar) and counting them on a FACS for 30 seconds.

EXAMPLE 14

Inhibition of Eotaxin Mediated Chemotaxis of Human Eosinophils—In Vitro Assay

The ability of compounds of the invention to inhibit eotaxin mediated chemotaxis of human eosinophils can be assessed using a slight modification of procedure described in Carr, M. W. et al., *Proc. Natl. Acad. Sci. USA*, 91:3652–56 (1994). Experiments are performed using 24 well chemotaxis plates (Costar Corp., Cambridge, Mass.). Eosinophils are isolated from blood using the procedure described in PCT Application WO96/22371. The endothelial cells used are the endothelial cell line ECV 304 obtained from European Collection of Animal Cell Cultures (Porton Down, Salisbury, U.K.). Endothelial cells are cultured on 6.5 mm diameter Biocoat.R™ Transwell tissue culture inserts (Costar Corp., Cambridge, Mass.) with a 3.0 µm pore size. Culture media for ECV 304 cells consists of M199, 10% Fetal Calf Serum, L-glutamine and antibiotics. Assay media consists of equal parts RPMI 1640 and M199, with 0.5% BSA. 24 hours before the assay 2×10⁵ ECV 304 cells are plated on each insert of the 24-well chemotaxis plate and incubated at 37° C. 20 nM of eotaxin diluted in assay medium is added to the bottom chamber. The final volume in bottom chamber is 600 µl. The endothelial coated tissue culture inserts are inserted into each well. Eosinophil cells (10⁶) suspended in 100 µl assay buffer are added to the top chamber. Test compounds dissolved in DMSO are added to both top and bottom chambers such that the final DMSO volume in each well was 0.5%. The assay is performed against two sets of controls. The positive control contains cells in the top chamber and eotaxin in the lower chamber. The negative control contains cells in the top chamber and only assay buffer in the lower chamber. The plates are incubated at 37° C. in 5% CO₂/95% air for 1–1.5 hours.

The cells that migrate to the bottom chamber are counted using flow cytometry. 500 µl of the cell suspension from the lower chamber are placed in a tube, and relative cell counts are obtained by acquiring events for a set time period of 30 seconds.

EXAMPLE 15

Inhibition of Eosinophil Influx into the Lungs of Ovalbumin Sensitized Balb/c Mice by CCR-3 Antagonist—In Vivo Assay The ability of the compounds of the invention to inhibit leukocyte infiltration into the lungs can be determined by measuring the inhibition of eosinophil accumulation into the bronchioalveolar lavage (BAL) fluid of Ovalbumin (OA)-sensitized balb/c mice after antigen challenge by aerosol. Briefly, male balb/c mice weighing 20–25 g are sensitized with OA (10 µg in 0.2 ml aluminum hydroxide solution) intraperitoneally on days 1 and 14. After a week, the mice are divided into ten groups. Test compound or only vehicle (control group) or anti-eotaxin antibody (positive control group) is administered either intraperitoneally, subcutaneously or orally. After 1 hour, the mice are placed in a Plexiglass box and exposed to OA aerosol generated by a PARISTAR™ nebulizer (PARI, Richmond, Va.) for 20 minutes. Mice which have not been sensitized or challenged are included as a negative control. After 24 or 72 hours, the mice are anesthetized (urethane, approx. 1 g/kg, i.p.), a tracheal cannula (PE 60 tubing) is inserted and the lungs are lavaged four times with 0.3 ml PBS. The BAL fluid is transferred into plastic tubes and kept on ice. Total leukocytes in a 20 µl aliquot of the BAL fluid is determined by Coulter Counter.™. (Coulter, Miami, Fla.). Differential leukocyte counts are made on Cytospin.™ preparations which have been stained with a modified Wright's stain (DiffQuick.™.) by light microscopy using standard morphological criteria.

The invention claimed is:
1. A compound having the formula:

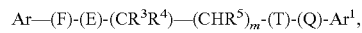

wherein:
T is

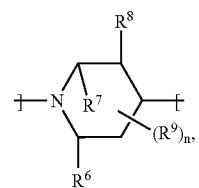

where $R^6$ is taken together with one of $R^7$ and $R^8$ to form a bridge of one to two carbon atoms, and the other of $R^7$ and $R^8$ is selected from hydrogen and $R^9$;

Ar and $Ar^1$ are each optionally substituted phenyl;

F is alkylene, alkenylene, or a bond;

E is selected from —C(=O)N($R^{10}$)—, —SO₂N($R^{10}$)—, —N($R^{11}$)C(=O)N($R^{10}$)—, —N($R^{11}$)SO₂N($R^{10}$)—, —N($R^{11}$)C(=S)N($R^{10}$)—, —N($R^{11}$)C(=O)—, —N($R^{11}$)SO₂—, —N($R^{12}$)C(=O)CH($R^{13}$)—, and CH($R^{13}$)C(=O)N($R^{12}$)—, where:

$R^{10}$, $R^{11}$, $R^{12}$, and $R^{13}$ are, independently of each other, hydrogen, alkyl, acyl, haloalkyl, cycloalkyl, cycloalkylalkyl, aryl, aralkyl, aralkenyl, heteroaryl, heteroaralkyl, heterocycloalkyl, heteroalkyl, or -(alkylene)-C(=O)-Z, where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

or alternatively, $R^{12}$ and $R^{13}$ may be taken together with the nitrogen and carbon atoms to which they are attached, respectively, to form a heterocyclyl or heteroaryl ring optionally substituted with up to two groups selected from $R^{14}$;

$R^3$ and $R^4$ are, independently of each other, hydrogen, alkyl, alkenyl, haloalkyl, cycloalkyl, cycloalkylalkyl, aryl, aralkyl, heteroaryl, heteroaralkyl, heterocyclyl, heterocyclylalkyl, heteroalkyl, -(alkylene)-C(=O)-$Z^1$, or -(alkylene)-C(O)$_2Z^1$, where $Z^1$ is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

$R^5$ is hydrogen or alkyl;

Q is —C(=O)— or $C_{1-2}$alkylene;

$R^9$ is attached to any available carbon atom of ring T and is selected from lower alkyl, hydroxy, lower alkoxy, halo, cyano, trifluoromethyl, trifluoromethoxy, or a lower alkyl substituted with one of hydroxy, lower alkoxy, halo, cyano, trifluoromethyl, or trifluoromethoxy;

$R^{14}$ is selected from lower alkyl, hydroxy, lower alkoxy, halo, cyano, trifluoromethyl, trifluoromethoxy, and a lower alkyl substituted with one of hydroxy, lower alkoxy, halo, cyano, trifluoromethyl, or trifluoromethoxy;

m is 0 or 1; and n is 0 to 4; and or a pharmaceutically acceptable salt thereof.

2. A compound according to claim 1, or a pharmaceutically acceptable salt thereof, wherein:

Ar and $Ar^1$ are both phenyl;

F is a bond;

E is selected from —C(=O)N($R^{10}$)—, —N($R^{11}$)C(=O)N($R^{10}$)—, —N($R^{11}$)C(=O)—, —N($R^{12}$)C(=O)CH($R^{13}$)—, and CH($R^{13}$)C(=O)N($R^{12}$)—, where:

$R^{10}$, $R^{11}$, $R^{12}$, and $R^{13}$ are, independently of each other, hydrogen or alkyl;

or alternatively, $R^{12}$ and $R^{13}$ may be taken together with the nitrogen and carbon atoms to which they are attached, respectively, to form a heterocyclyl or heteroaryl ring optionally substituted with up to two groups selected from $R^{14}$;

$R^3$ and $R^4$ are, independently of each other, hydrogen, alkyl, alkenyl, haloalkyl, heteroalkyl, or -(alkylene)-C(=O)-$Z^1$, where $Z^1$ is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

Q is —CH$_2$—;

$R^9$ and $R^{14}$ are independently selected from methyl, ethyl, hydroxy, methoxy, halo, cyano, trifluoromethyl, or trifluoromethoxy; and n is 0 to 2.

3. A compound according to claim 1, or a pharmaceutically acceptable salt thereof, wherein T is selected from the group consisting of:

and $R^9$ is attached to any available carbon atom of ring T and is selected from lower alkyl and hydroxy, and n is 0 to 2.

4. A compound of claim 1, or a pharmaceutically acceptable salt thereof, wherein:

Ar is a phenyl ring optionally substituted with one, two or three substituents selected from alkyl, heteroalkyl, alkoxy, —COR$^{15}$, —SO$_2$R$^{17}$, methylenedioxy, hydroxy, halo, acylamino, amino, mono- or disubstituted amino, —CONR$^{15}$R$^{16}$, -(alkylene)-CONR$^{15}$R$^{16}$, —COOR$^{15}$, -(alkylene)-COOR$^{15}$ and/or —NR$^{16}$SO$_2$R$^{17}$;

$R^{15}$ and $R^{16}$ are each independently hydrogen or alkyl; and $R^{17}$ is alkyl, amino or mono or disubstituted amino.

5. A compound of claim 4, or a pharmaceutically acceptable salt thereof, wherein Ar is selected from phenyl, 4-chlorophenyl, 4-methylphenyl, 4-methoxyphenyl, 3-methylsulfonylphenyl, 3,5-dimethoxyphenyl, 3,4-dimethoxyphenyl, and 3,4,5-trimethoxyphenyl.

6. A compound of claim 1, or a pharmaceutically acceptable salt thereof, wherein F is a bond.

7. A compound of claim 1, or a pharmaceutically acceptable salt thereof, wherein E is —C(=O)N($R^{10}$)—, —N($R^{10}$)C(=O)N($R^{11}$)—, or N($R^{12}$)C(=O)CH($R^{13}$)—, where $R^{10}$ and $R^{11}$ are hydrogen or lower alkyl, and $R^{12}$ and $R^{13}$ are taken together with the nitrogen and carbon atoms to which they are attached, respectively, to form where $R^{18}$ and $R^{19}$ are selected from hydrogen and lower alkyl.

8. A compound of claim 7, or a pharmaceutically acceptable salt thereof, wherein
E is

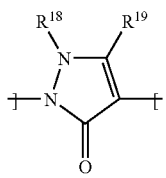

and m is 0.

9. A compound of claim 1, or a pharmaceutically acceptable salt thereof, wherein
$R^3$ is hydrogen; and
$R^4$ is hydrogen, methyl, ethyl, 1-methylethyl, isopropyl, 1-hydroxyethyl or 2-hydroxyethyl.

10. A compound of claim 1, or a pharmaceutically acceptable salt thereof, wherein
$R^3$ is hydrogen; and $R^4$ is 1-methylethyl.

11. A compound of claim 1, or a pharmaceutically acceptable salt thereof, wherein T is

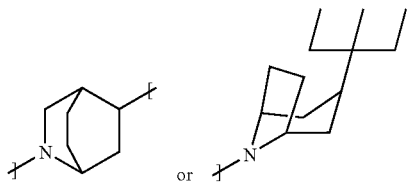

12. A compound of claim 1, or a pharmaceutically acceptable salt thereof, wherein Q is —CH$_2$—.

13. A compound of claim 1, or a pharmaceutically acceptable salt thereof, wherein:
$Ar^1$ is a phenyl ring optionally substituted with one, two or three substituent selected from alkyl, heteroalkyl, alkoxy, halo, trifluoromethyl, nitro, or mono- or disubstituted amino.

14. A compound of claim 1, or a pharmaceutically acceptable salt thereof, wherein:
$Ar^1$ is 4-chlorophenyl or 3,4-dichlorophenyl.

15. A compound having the formula (II):

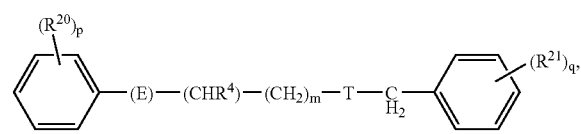

(II)

or a pharmaceutically-acceptable salt thereof, in which:
T is

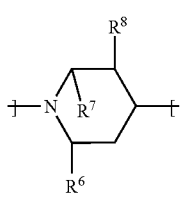

where $R^6$ is taken together with one of $R^7$ and $R^8$ to form a bridge of one to two carbon atoms optionally substituted with one to two CH$_3$, and the other of $R^7$ and $R^8$ is selected from hydrogen and lower alkyl;
E is selected from —C(=O)N(R$^{10}$)—, —N(R$^{11}$)C(=O)N(R$^{10}$)—, and —N(R$^{12}$)C(=O)CH(R$^{13}$)—, where:
$R^{10}$, $R^{11}$, $R^{12}$, and $R^{13}$ are independently of each other hydrogen or lower alkyl, or alternatively, $R^{12}$ and $R^{13}$ may be taken together with the nitrogen and carbon atoms to which they are attached, respectively, to form a five-membered heterocyclyl or heteroaryl ring having up to two N atoms and optionally substituted with up to two groups selected from methyl, ethyl, hydroxy, methoxy, halo, cyano, trifluoromethyl, and trifluoromethoxy;
is $R^4$ is hydrogen, lower alkyl, or lower alkyl substituted with hydroxy;
$R^{20}$ and $R^{21}$ are each independently selected from halo, OR$^{22}$, and SO$_2$R$^{22}$, wherein R$^{22}$ is lower alkyl;
m is 0 or 1;
p and q are independently 0, 1, 2 or 3.

16. A compound of claim 15, or a pharmaceutically acceptable salt thereof, wherein
E is selected from —C(=O)NH—, —NHC(=O)NH—, and

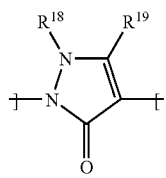

where $R^{18}$ and $R^{19}$ are each hydrogen or lower alkyl;
$R^4$ is hydrogen, methyl, ethyl, 1-hydroxyethyl, or 1-methylethyl;
$R^6$ is taken together with one of $R^7$ and $R^8$ to form a bridge of two carbon atoms and the other of $R^7$ and $R^8$ is hydrogen;
$R^{20}$ is selected from halo, methoxy, and methylsulfonyl;
$R^{21}$ is halo;
p is 0, 1, 2 or 3; and
q is 0, 1, or 2.

17. A compound of claim 16, or a pharmaceutically acceptable salt, wherein T is

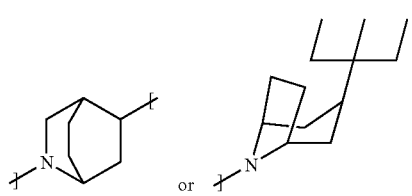

18. A pharmaceutical composition comprising a therapeutically effective amount of a compound of claim 1 and a pharmaceutically acceptable excipient.

* * * * *